US009744293B2

(12) United States Patent
Abdulreda et al.

(10) Patent No.: US 9,744,293 B2
(45) Date of Patent: Aug. 29, 2017

(54) SYSTEM AND METHODS FOR MOTORIZED INJECTION AND ASPIRATION

(76) Inventors: Midhat H. Abdulreda, Hollywood, FL (US); Per-Olof Berggren, Solina (SE); Conrado Freites, Miami, FL (US)

( * ) Notice: Subject to any disclaimer, the term of this patent is extended or adjusted under 35 U.S.C. 154(b) by 750 days.

(21) Appl. No.: 13/469,327

(22) Filed: May 11, 2012

(65) Prior Publication Data

US 2012/0289891 A1    Nov. 15, 2012

Related U.S. Application Data

(60) Provisional application No. 61/485,793, filed on May 13, 2011, provisional application No. 61/534,516, filed on Sep. 14, 2011.

(51) Int. Cl.
*A61M 5/20* (2006.01)
*A61M 5/145* (2006.01)
(Continued)

(52) U.S. Cl.
CPC ........ *A61M 5/1456* (2013.01); *A61M 1/0058* (2013.01); *A61M 5/1458* (2013.01);
(Continued)

(58) Field of Classification Search
CPC ................ A61M 5/142; A61M 1/0058; A61M 2005/1403; A61M 2209/01; A61M 5/1452; A61M 5/172; A61M 1/0031; A61M 5/1456; A61M 5/1458; A61M 5/3148; A61M 2205/586; A61M 1/0062
(Continued)

(56) References Cited

U.S. PATENT DOCUMENTS 3,833,782 A * 9/1974 Bartel ................... H01C 10/16
                                                          200/86.5
4,428,748 A * 1/1984 Peyman .............. A61F 9/00745
                                                          433/119
(Continued)

FOREIGN PATENT DOCUMENTS

FR           2735031        12/1996
JP        2001171544         6/2001
(Continued)

OTHER PUBLICATIONS

ISR and Written Opinion for PCT/US2012/037434, mailed Aug. 27, 2012.
(Continued)

*Primary Examiner* — Nathan R Price
*Assistant Examiner* — Anh Bui
(74) *Attorney, Agent, or Firm* — McDonnell Boehnen Hulbert & Berghoff LLP

(57) ABSTRACT

A motorized injection and aspiration system and methods for its use, where the motorized injection and aspiration system comprises (a) a syringe coupled to a needle, wherein the syringe includes a plunger, (b) a cannula, (c) a tube having first and second ends, wherein the first end is coupled to the needle and the second end is coupled to the cannula, (d) a syringe driver to drive the plunger, (e) at least one foot pedal, (f) a step motor, and (g) a control unit in communication with the step motor, the syringe driver and the at least one foot pedal.

22 Claims, 7 Drawing Sheets

(51) Int. Cl.
*A61M 1/00* (2006.01)
*A61M 5/31* (2006.01)
*A61B 17/00* (2006.01)

(52) U.S. Cl.
CPC . *A61M 5/3148* (2013.01); *A61B 2017/00973* (2013.01); *A61B 2017/00977* (2013.01); *A61M 1/0062* (2013.01); *A61M 2205/586* (2013.01); *A61M 2209/01* (2013.01)

(58) Field of Classification Search
USPC .............. 604/19, 22, 30–31, 35–36, 38, 43, 604/151–156, 246, 523, 533–534
See application file for complete search history.

(56) References Cited

U.S. PATENT DOCUMENTS

| | | | |
|---|---|---|---|
| 4,764,165 A | | 8/1988 | Reimels et al. |
| 4,790,823 A | | 12/1988 | Charton et al. |
| 5,180,371 A | * | 1/1993 | Spinello ................. A61C 19/08 |
| | | | 604/118 |
| 6,113,574 A | * | 9/2000 | Spinello ............ A61M 5/14566 |
| | | | 128/DIG. 12 |
| 6,221,045 B1 | | 4/2001 | Duchon et al. |
| 6,290,690 B1 | | 9/2001 | Huculak et al. |
| 6,887,216 B2 | | 5/2005 | Hochman et al. |
| 6,945,954 B2 | | 9/2005 | Hochman et al. |
| 7,625,354 B2 | * | 12/2009 | Hochman ........... A61M 5/1456 |
| | | | 137/68.11 |
| 9,048,508 B2 | | 6/2015 | Kato et al. |
| 9,050,123 B2 | | 6/2015 | Krause et al. |
| 9,231,277 B2 | | 1/2016 | Kato et al. |
| 2003/0078534 A1 | * | 4/2003 | Hochman ........... A61M 5/1456 |
| | | | 604/67 |
| 2003/0167021 A1 | * | 9/2003 | Shimm ............. A61M 5/14526 |
| | | | 600/554 |
| 2004/0074318 A1 | * | 4/2004 | DiTrolio ................. B01L 3/021 |
| | | | 73/864.15 |
| 2007/0060898 A1 | * | 3/2007 | Shaughnessy ........ A61M 39/10 |
| | | | 604/284 |
| 2008/0114290 A1 | | 5/2008 | King et al. |
| 2009/0060843 A1 | | 3/2009 | Berggren et al. |
| 2009/0099520 A1 | * | 4/2009 | Millman et al. .............. 604/131 |

FOREIGN PATENT DOCUMENTS

| | | |
|---|---|---|
| JP | 2004312456 | 11/2004 |
| JP | 2009011326 | 1/2009 |
| JP | 201005565 | 1/2010 |
| JP | 2011104164 | 6/2011 |

OTHER PUBLICATIONS

Cejvan et al., Diabetes 52:1176-1181 (2003).
Zambre et al., Biochem. Pharmacol. 57:1159-1164 (1999).
Fagan et al., Surgery 124:254-259 (1998).
Abdulreda, M.H., Faleo, G., Molano, R.D., Lopez-Cabezas, M., Molina, J., Tan, Y., Echeverria, O.A., Zahr-Akrawi, E., Rodriguez-Diaz, R., Edlund, P.K., et al. (2011). High-resolution, noninvasive longitudinal live imaging of immune responses. In Proc Natl Acad Sci U S A. pp. 1-6.
Aswathy, R.G. Yoshida, Y., Maekawa, T., and Kumar, D.S. (2010). Near-infrared quantum dots for deep tissue imaging. Anal Bioanal Chem 397, 1417-1435.
Cahalan, M.D., and Parker, I. (2008). Choreography of cell motility and interaction dynamics imaged by two-photon microscopy in lymphoid organs. Annu Rev Immunol 26, 585-626.
Celli, S., Albert, M.L., and Bousso, P. (2011). Visualizing the innate and adaptive immune responses underlying allograft rejection by two-photon microscopy. Nat Med. pp. 744-749.
Coppieters, K., Martinic, M.M., Kiosses, W.B., Amirian, N., and von Herrath, M. (2010). A novel technique for the in vivo imaging of autoimmune diabetes development in the pancreas by two-photon microscopy. PLoS One 5, e15732 , pp. 1-8.
Denk, W., Delaney, K.R., Gelperin, A., Kleinfeld, D., Strowbridge, B.W., Tank, D.W., and Yuste, R. (1994). Anatomical and functional imaging of neurons using 2-photon laser scanning microscopy. J Neurosci Methods 54, 151-162.
Denk, W., Strickler, J.H., and Webb, W.W. (1990). Two-photon laser scanning fluorescence microscopy. Science 248, 73-76.
Fan, Z., Spencer, J., Lu, Y., Pitsillides, C., Singh, G., Kim, P., Yun, S., Toxavidis, V., Strom, T., Lin, C., et al. (2010). In vivo tracking of 'color-coded' effector, natural and induced regulatory T cells in the allograft response. Nat Med 16, 718-722.
Ghoroghchian, P.P., Therien, M.J., and Hammer, D.A. (2009). In vivo fluorescence imaging: a personal perspective. Wiley Interdiscip Rev Nanomed Nanobiotechnol 1, 156-167.
Khorshidi, M.A., Vanherberghen, B., Kowalewski, J.M., Garrod, K.R., Lindstrom, S., Andersson-Svahn, H., Brismar, H., Cahalan, M.D., and Onfelt, B. (2011). Analysis of transient migration behavior of natural killer cells imaged in situ and in vitro. Integr Biol (Camb) 3, 770-778.
Leblond, F., Davis, S., Valdés, P., and Pogue, B. (2010). Pre-clinical whole-body fluorescence imaging: Review of instruments, methods and applications. J Photochem Photobiol B 98, 77-94.
Leibiger, I.B., Caicedo, A., and Berggren, P.O. (2011). Non-invasive in vivo imaging of pancreatic β-cell function and survival—a perspective. Acta Physiol (Oxf), pp. 178-185.
Martinic, M.M., and von Herrath, M.G. (2008). Real-time imaging of the pancreas during development of diabetes. Immunol Rev 221, 200-213.
Matheu, M.P., Cahalan, M.D., and Parker, I. (2011). Immunoimaging: studying immune system dynamics using two-photon microscopy. Cold Spring Harb Protoc 2011, pp. 147-155.
Mostany, R., and Portera-Cailliau, C. (2008). A method for 2-photon imaging of blood flow in the neocortex through a cranial window. J Vis Exp. 1-2.
Ntziachristos, V. (2010). Going deeper than microscopy: the optical imaging frontier in biology. In Nat Methods (United States), pp. 603-614.
Pileggi, A., Molano, R.D., Berney, T., Cattan, P., Vizzardelli, C., Oliver, R., Fraker, C., Ricordi, C., Pastori, R.L., Bach, F.H., et al. (2001). Heme oxygenase-1 induction in islet cells results in protection from apoptosis and improved in vivo function after transplantation. Diabetes 50, 1983-1991.
Prescher, A., Mory, C., Martin, M., Fiedler, M., and Uhlmann, D. (2010). Effect of FTY720 treatment on postischemic pancreatic microhemodynamics. Transplant Proc 42, 3984-3985.
Sabek, O., Gaber, M.W., Wilson, C.M., Zawaski, J.A., Fraga, D.W., and Gaber, O. (2010). Imaging of human islet vascularization using a dorsal window model. In Transplant Proc (United States: Published by Elsevier Inc.), pp. 2112-2114.
Speier, S., Nyqvist, D., Cabrera, O., Yu, J., Molano, R.D., Pileggi, A., Moede, T., Köhler, M., Wilbertz, J., Leibiger, B., et al. (2008a). Noninvasive in vivo imaging of pancreatic islet cell biology. Nat Med 14, 574-578.
Speier, S., Nyqvist, D., Kohler, M., Caicedo, A., Leibiger, I.B., and Berggren, P.O. (2008b). Noninvasive high-resolution in vivo imaging of cell biology in the anterior chamber of the mouse eye. Nat Protoc 3, 1278-1286.
Toso, C., Vallee, J.P., Morel, P., Ris, F., Demuylder-Mischler, S., Lepetit-Coiffe, M., Marangon, N., Saudek, F., James Shapiro, A.M., Bosco, D., et al. (2008). Clinical magnetic resonance imaging of pancreatic islet grafts after iron nanoparticle labeling. Am J Transplant 8, 701-706.
Wang, B.G., Konig, K., and Halbhuber, K.J. (2010a). Two-photon microscopy of deep intravital tissues and its merits in clinical research. J Microsc 238, 1-20.
Wang, Y., Maslov, K., Kim, C., Hu, S., and Wang, L. (2010b). Integrated photoacoustic and fluorescence confocal microscopy. IEEE Trans Biomed Eng 57, 2576-2578.
Weigert, R., Sramkova, M., Parente, L., Amornphimoltham, P., and Masedunskas, A. (2010). Intravital microscopy: a novel tool to study cell biology in living animals. Histochem Cell Biol 133, 481-491.

(56) References Cited

OTHER PUBLICATIONS

Abdulreda, M.H., Faleo, G., Molano, R.D., Lopez-Cabezas, M., Molina, J., Tan, Y., Echeverria, O.A., Zahr-Akrawi, E., Rodriguez-Diaz, R., Edlund, P.K., et al. (2011). High-resolution, noninvasive longitudinal live imaging of immune responses. In Proc. Natl Acad Sci U S A. pp. 1-6.

Aswathy, R.G., Yoshida, Y., Maekawa, T., and Kumar, D.S. (2010). Near-infrared quantum dots for deep tissue imaging. Anal Bioanal Chem 397, 1417-1435.

Celli, S., Albert, M.L., and Bousso, P. (2011). Visualizing the innate and adaptive immune responses underlying allograft rejection by two-photon microscopy. Nat Med., pp. 744-749.

Coppieters, K., Martinic, M.M., Kiosses, W.B., Amirian, N., and von Herrath, M. (2010). A novel technique for the in vivo imaging of autoimmune diabetes development in the pancreas by two-photon microscopy. PLoS One 5, e15732, pp. 1-8.

Leibiger, I.B., Caicedo, A., and Berggren, P.O. (2011). Non-invasive in vivo imaging of pancreatic-cell function and survival—a perspective. Acta Physiol (Oxf), pp. 178-185.

Prescher, A., Mory, C., Martin, M., Fiedler, M., and Uhlmann, D. (2010). Effect of FTY720 treatment on postischemic pancreatic microhemodynamics Transplant Proc 42, 3984-3985.

\* cited by examiner

SYSTEM AND METHODS FOR MOTORIZED INJECTION AND ASPIRATION

CROSS-REFERENCE

This application claims priority to U.S. Provisional Patent Application Ser. No. 61/485,793 filed May 13, 2011 and 61/534,516 filed Sep. 14, 2011, each of which is incorporated by reference herein in its entirety.

STATEMENT OF U.S. GOVERNMENT INTEREST

This invention was made with government support under Grant Nos. F32DK083226 and 5U01DK070460-07 awarded by the National Institutes of Health. The U.S. government has certain rights in the invention.

BACKGROUND OF THE INVENTION

Micro-procedures, such as micro-surgery or micro-manipulation, in experimental and/or clinical settings at times require both injection and aspiration of fluids or solutions. Currently available syringe pumps work either in a single injection or aspiration mode. These systems require the user to stop/pause in the middle of a procedure and let go of the specimen or animal, when this may not be possible or desirable, in order to reprogram the control unit to switch modes. Further, reprogramming the control unit in the middle of a procedure is impractical since the operator's hands are typically not free. Moreover, while these systems can deliver preset volumes at preset flow rates, these parameters cannot be changed in real time during injection or aspiration.

In addition, some current systems enable both aspiration and infusion modes using two terminals (i.e., two needles, two cannulas, etc. . . . ), which requires two incisions or entry/exit points. In operation both the injection and aspiration modes are performed simultaneously even when a single mode is desired or required. As a result, these systems do not enable aspiration and/or delivery of the same tissue or liquid. And the preset volumes and flow rates likewise cannot be changed during injection or aspiration.

SUMMARY OF THE INVENTION

The present invention provides a motorized injection and aspiration system that allows for an immediate transition between the actions of injection and aspiration through a single entry point without interruption at any time during the operation and as many times as desired through the use of one or more foot pedals. The motorized injection and aspiration system has the additional benefit of adjusting the flow rate and volume of working fluid to be aspirated or injected via the same one or more foot pedals. This system accomplishes controlled and precise aspiration and delivery of solutions of macro- and micro-particles into confined spaces with minimal turbulence and physical disturbance, which in turn reduces the waste of precious and expensive reagents. Yet another improvement of the system is that the components in contact with the specimen and the solution are autoclavable to prevent contamination in sterile applications. A further advantage of the system is that in operation it is hands-free, enabling a single person to perform procedures, such as transplantations, which are typically performed by two people.

Example applications of the invention include experimental microsurgery or micromanipulation in the areas of transplantation (to infuse pancreatic islets and pancreatic embryonic buds, and cell suspensions into different sites in living organisms or mammals), cochlear perfusion (to deliver pharmacological agents and aspirate cochlear fluids, for example perilymph), flushing of implantable microdevices, such as catheters, and lines, etc., steriotaxic delivery and aspiration with a single cannula in a brain, and infusion and withdrawal of solutions and cells/tissues in culture. In the clinical setting, microprocedures intraocular delivery and withdrawal with a single cannula, clinical pancreatic islet infusion, flush of and withdrawal from middle ear and other cranial cavities using a single cannula.

Thus, in a first aspect, the present invention provides a motorized injection and aspiration system comprising: (a) a syringe coupled to a needle, wherein the syringe includes a plunger, (b) a cannula, (c) a tube having first and second ends, wherein the first end is coupled to the needle and the second end is coupled to the cannula, (d) a syringe driver to drive the plunger, (e) at least one foot pedal, (f) a step motor, and (g) a control unit in communication with the step motor, the syringe driver and the at least one foot pedal.

In one embodiment, the invention provides that the at least one foot pedal comprises a first foot pedal and a second foot pedal, such that the first foot pedal controls an injection mode and the second foot pedal controls an aspiration mode.

In a further embodiment, the first foot pedal includes a potentiometer to control the injection flow rate and the second foot pedal includes a potentiometer to control the aspiration flow rate.

In a second aspect, the present invention also provides a method for utilizing the motorized injection and aspiration system, where the method comprises: (a) loading a syringe driver with a syringe, wherein the syringe is prefilled with a solution and wherein the syringe comprises a syringe body, a plunger, and a needle; wherein the syringe driver comprises (i) a base for holding the syringe body in a static position and (ii) a moveable platform for receiving the plunger, (b) rotating a first foot pedal forward from a resting position, (c) in response, driving the plunger forward via the moveable platform in an injection mode, (d) rotating a second foot pedal forward from the resting position, and (e) in response, driving the plunger backward via the moveable platform in an aspiration mode.

In one embodiment the method further comprises the step of coupling a first end of a tube to the needle and a second end of the tube to a cannula.

In another embodiment the method further comprises the step of adjusting an injection flow rate by changing the degree of rotation of the first foot pedal.

In a further embodiment the method further comprises the step of adjusting an aspiration flow rate by changing the degree of rotation of the second foot pedal.

In a third aspect, the present invention provides a method for utilizing the motorized injection and aspiration system, where the method comprises: (a) loading syringe driver with a syringe, wherein the syringe is prefilled with a solution and wherein the syringe comprises a syringe body, a plunger, and a needle, and wherein the syringe driver comprises (i) a base for holding a syringe body in a static position and (ii) a moveable platform for receiving the syringe plunger, (b) rotating a single foot pedal forward from a resting position, (c) in response, driving the plunger forward via the moveable platform in an injection mode, (d) rotating the single foot pedal backward from a resting position, and (e) in response, driving the plunger backward via the moveable platform in an aspiration mode.

In one embodiment, the method further comprises the step of adjusting the injection flow rate by altering the degree of the foot pedal's forward rotation and adjusting the aspiration flow rate by altering the degree of the foot pedal's backward rotation.

In a fourth aspect, the present invention provides a method for utilizing the motorized injection and aspiration system, where the method comprises: (a) loading a syringe into a syringe driver, wherein the syringe is prefilled with a solution, and wherein the syringe comprises a syringe body, a plunger, and a needle, and wherein the syringe driver comprises (i) a base for holding the syringe body in a static position and (ii) a moveable platform for receiving the plunger, (b) rotating the first foot pedal forward from a resting position, (c) in response, driving the plunger forward via the moveable platform in an injection mode, (d) rotating the second foot pedal forward from a resting position, and (e) in response, driving the plunger backward via the moveable platform in an aspiration mode.

In a fifth aspect, the present invention provides a method for utilizing the motorized injection and aspiration system, where the method comprises: (a) loading a syringe driver with a syringe, wherein the syringe is prefilled with a solution, and wherein the syringe comprises a syringe body, a plunger, and a needle, and wherein the syringe driver comprises a base for holding a syringe body in a static position and a moveable platform for receiving the syringe plunger, (b) rotating the single foot pedal forward from a resting position, (c) in response, driving the plunger forward via the moveable platform in an injection mode, (d) rotating the single foot pedal backward from a resting position, and (e) in response, driving the plunger backward via the moveable platform in an aspiration mode.

In a sixth aspect, the present invention provides a method for utilizing the motorized injection and aspiration system to perform cell transplantation into the anterior chamber of the eye, where the method comprises: (a) loading the syringe driver with a syringe, wherein the syringe is prefilled with a solution and wherein the syringe comprises a syringe body, a plunger, and a needle, and wherein the syringe driver comprises a base for holding the syringe body in a static position and a moveable platform for receiving the plunger, (b) aspirating a desired amount of cells into a reservoir using a syringe driver, (c) connecting the cannula to the reservoir via the connecting tube, (d) connecting the second end of the syringe tube to the needle, (e) loading the cannula with cells by pushing the cells out of the reservoir into the connecting tube and then into the cannula, (f) making an incision in the cornea of the eye of a subject, (g) inserting the cannula through the incision, (h) rotating the first foot pedal forward from a resting position, (i) in response, driving the plunger forward via the moveable platform in an injection mode, ejecting the cells out of the cannula and depositing the cells on the iris, (j) if necessary, rotating the second foot pedal forward from a resting position, (k) if necessary, in response, driving the plunger backward via the moveable platform in an aspiration mode, pulling the cells back into the cannula, and (l) retracting the cannula from the incision.

DETAILED DESCRIPTION OF THE INVENTION

Figure 1:
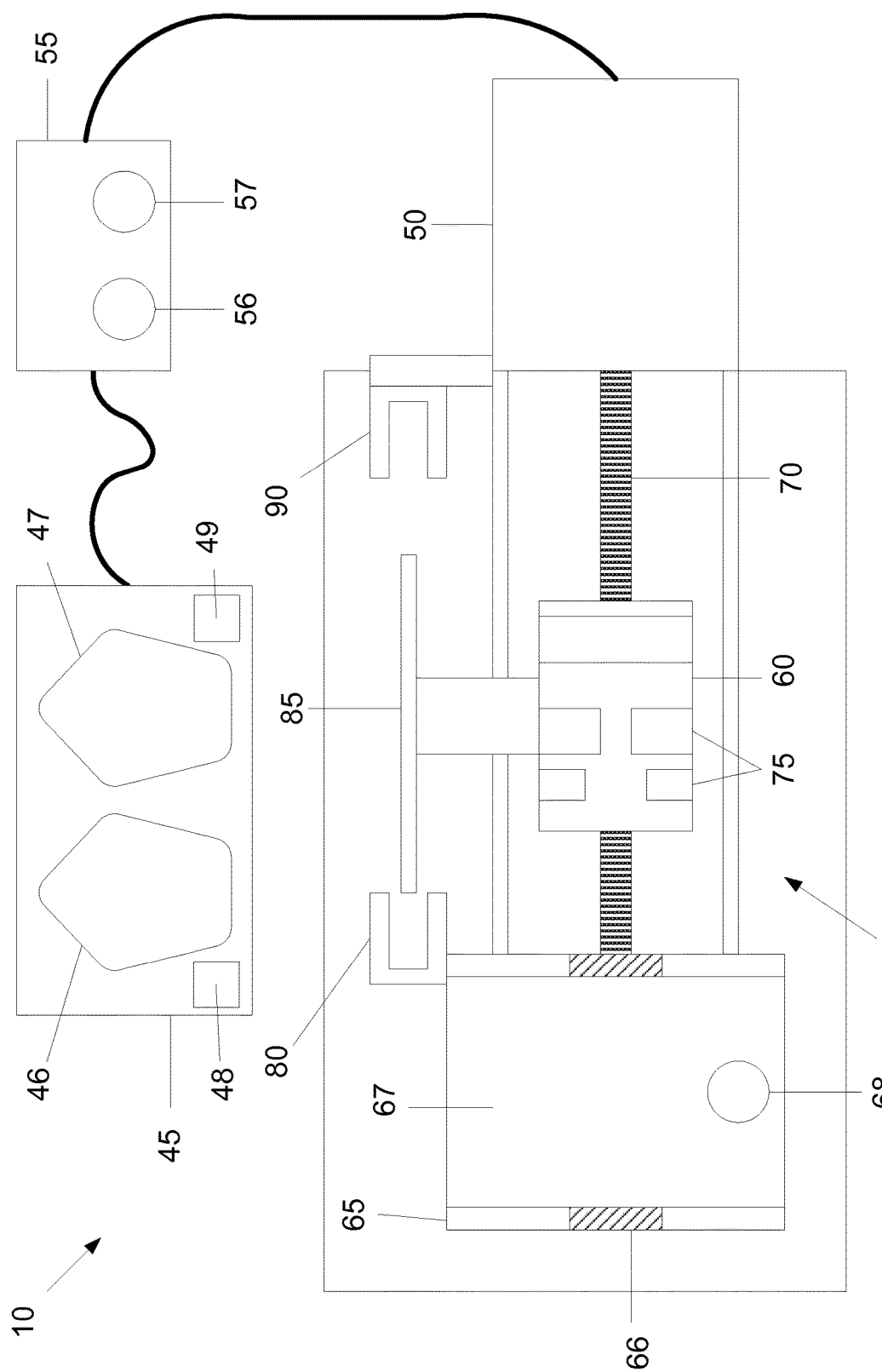
FIG. 1 is a top view of the motorized injection and aspiration system in an unloaded condition.
Figure 2:
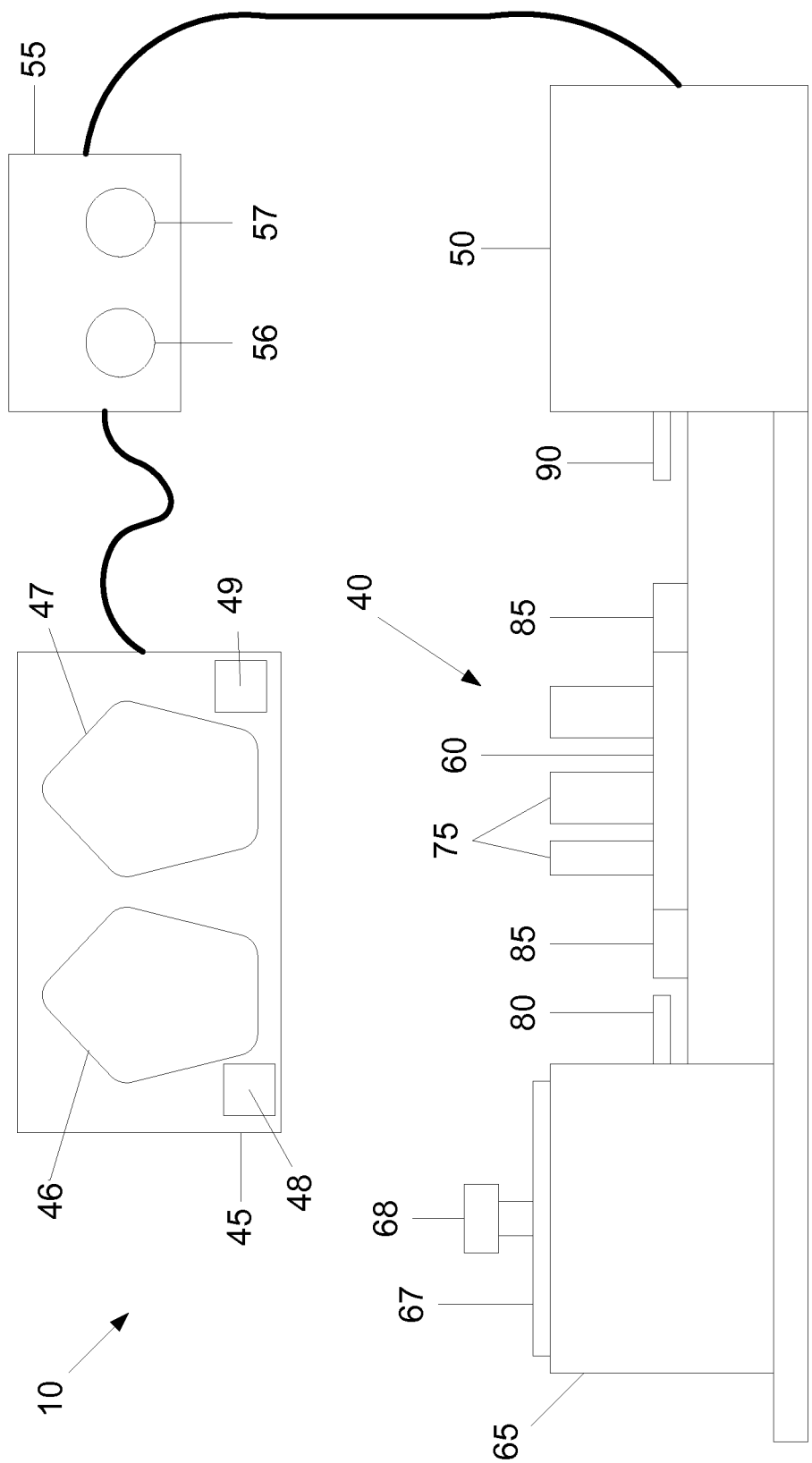
FIG. 2 is a side view of the motorized injection and aspiration system in an unloaded condition.
Figure 3:
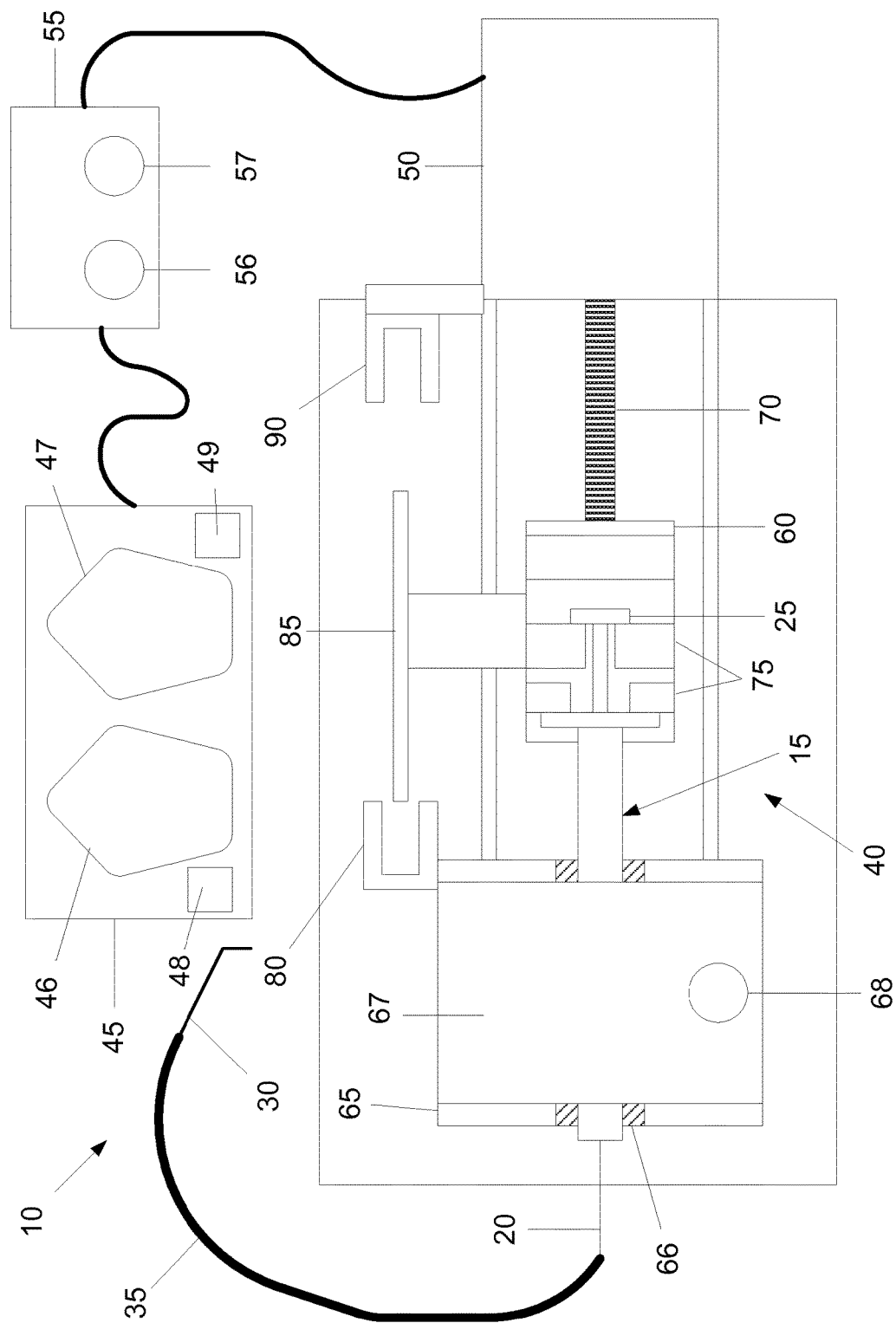
FIG. 3 is a top view of the motorized injection and aspiration system in a loaded condition.
Figure 4:
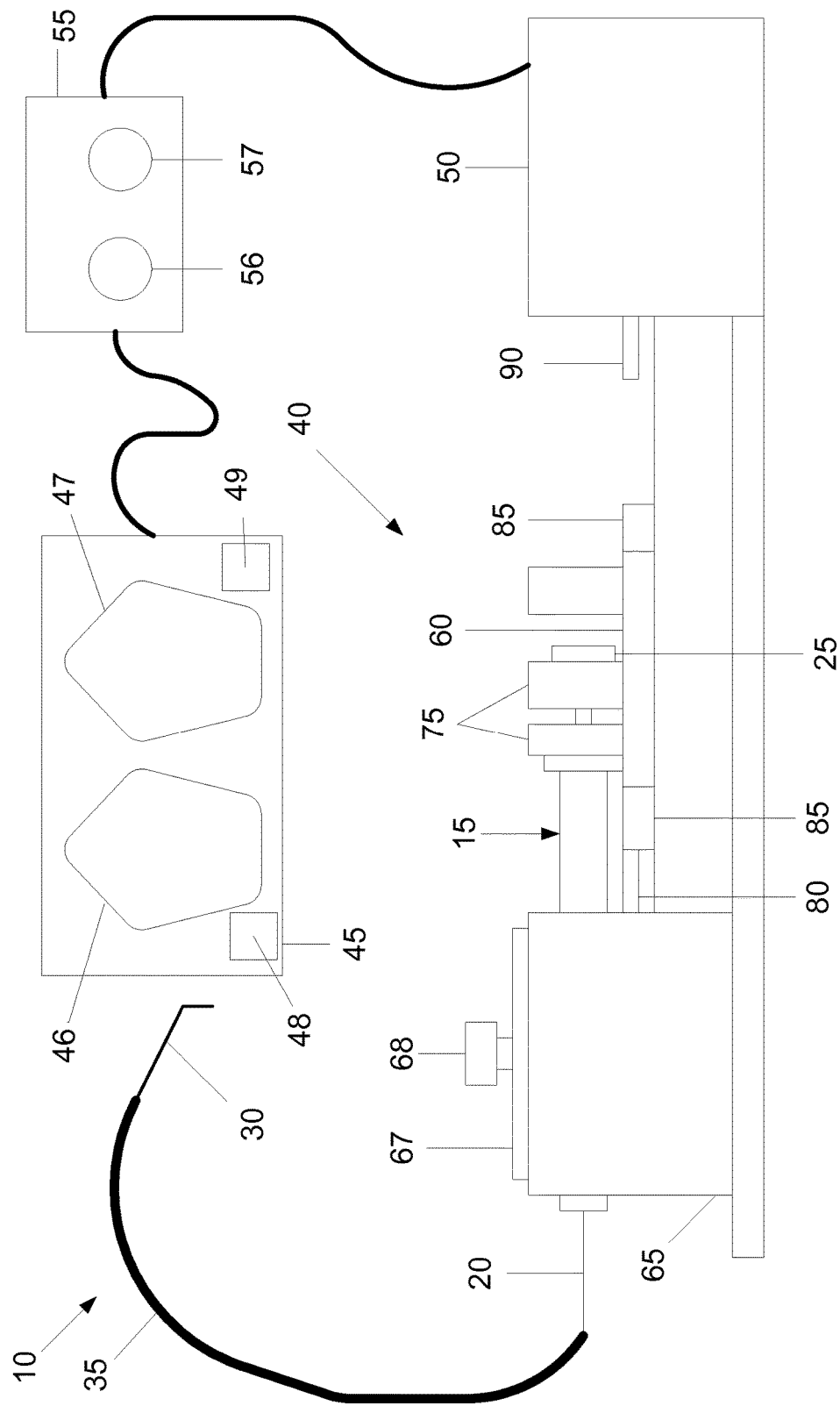
FIG. 4 is a side view of the motorized injection and aspiration system in a loaded condition.

In a first aspect, as shown in FIGS. 1-4, the present invention may take the form of a motorized injection and aspiration system 10 comprising: (a) a syringe 15 coupled to a needle 20, wherein the syringe includes a plunger 25, (b) a cannula 30, (c) a tube 35 having first and second ends, wherein the first end is coupled to the needle 20 and the second end is coupled to the cannula 30, (d) a syringe driver 40 to drive the plunger 25, (e) at least one foot pedal 45, (f) a step motor 50, and (g) a control unit 55 in communication with the step motor 50, the syringe driver 40 and the at least one foot pedal 45.

As used herein, "syringe" 15 means a tubular body with a plunger 25 disposed in one end and a needle 20 disposed in the opposing end. Any type or size of syringe could be used in operation, including disposable syringes. For example, small volume syringes would be appropriate to achieve small volume injections with a low flow rate. In a preferred embodiment, the syringe comprising a Luer-type syringe. There are two varieties of Luer Taper connections: Luer-Lok and Luer-Slip. Luer-Lok fittings have a threaded end that twists and locks with mating threads on a Luer-Lok needle. Luer-Slip fittings simply conform to Luer taper dimensions and are pressed together and held by friction (they have no threads).

As used herein, a "cannula" 30 is a narrow tube for insertion into the body to draw off/aspirate fluid or deliver/inject solutions, for example, in the form of fluids, reagents, cellular suspensions, cells/tissues in culture, pancreatic islets, pancreatic embryonic buds, and/or pharmacological agents.

As used herein, "tube" 35 refers to small diameter medical grade tubing, for example, Tygon™ Tubing. Any type of tubing of various diameters may be employed as long as it is made of a material compatible with the solution being injected and/or aspirated.

As used herein, a "syringe driver" 40 comprises a linear stage that includes a platform 60 and a base 65, joined by some form of guide or linear bearing 70 in such a way that the platform 60 is restricted to linear motion with respect to the base 65. The platform 60 defines a receptacle 75 sized and shaped to receive the syringe plunger 25, while the base 65 receives and holds the syringe body 15 substantially stationary. In one embodiment, the base 65 defines a channel 66 to receive the syringe body 15. A top plate 67 is then affixed to the base 65 by a set screw 68, for example, to hold the syringe 15 in place. In operation, as the step motor 50 is driven forward or backward by the foot pedal 45, the platform 60 reciprocally moves the plunger 25 forward and backward relative to the stationary syringe 15.

As used herein, a "step motor" 50 is an electromechanical device which converts electrical pulses into discrete mechanical movements such that it divides a full rotation into a large number of steps. These discrete movements are controlled through electrical command pulses which are generated by the rotation of the at least one foot pedal 45. Specifically, in a single foot pedal application, the rotation of the pedal forward determines that injection is occurring and rotation backward determines that aspiration is occurring or vice versa. Likewise the degree of the rotation forward dictates the flow rate of the injection and the degree of rotation backward dictates the flow rate of the aspiration. In a dual foot pedal application, the use of a first foot pedal 46 determines that the system is operating in an injection mode, while the use of a second foot pedal 47 determines that the system operates in an aspiration mode. The degree of rotation of the first and second foot pedals 46, 47 again governs the flow rate of the injection and aspiration.

As used herein, a dual "foot pedal" 46, 47 is the preferred embodiment. However, the same advantages can be achieved through the use of a single foot pedal 45 and therefore both embodiments will be discussed. In general, a foot pedal 45 is a rotatable lever that is operated with the foot and includes potentiometers 48, 49 that function as accelerators to increase the flow rate as the degree of rotation of the pedal increases from a resting position.

In the single foot pedal application 45, the pedal has a resting position from which it may be rotated forward and backward. When the foot pedal 45 is pressed forward, it is in, for example, the injection mode and the further forward it is rotated the faster the flow rate. Likewise, when the foot pedal 45 is rotated backward from the rest position, it enters the aspiration mode and the further backward it is rotated the faster the flow rate.

In the dual foot pedal 46, 47 application, there are two pedals that both rotate forward from a resting position. A first pedal 46 is dedicated to the injection mode and a second pedal 47 is dedicated to the aspiration mode or vice versa.

The speed of the flow rate for both injection and aspiration is controlled by the degree of forward rotation of each respective foot pedal (i.e. the greater the degree of rotation the greater the flow rate). The positioning of the first and second foot pedal relative to one another is interchangeable, meaning that the first foot pedal 46 may be either to the left or the right of the second foot pedal 47.

As used herein, the "control unit" 55 includes adjustable potentiometers 48, 49 that control the maximum speed of the motor 50. Specifically, the pedal potentiometers 48, 49 interface with a step motor driver contained in the control unit 55. The step motor driver translates the voltage generated by the potentiometer rotation angle of the at least one foot pedal 45 into electrical pulses that in turn translate to different speeds of the syringe driver 40, which controls the ultimate flow rate of the syringe. The interface between the at least one foot pedal and the control unit is preferably electrically hardwired, but could also be effected through wireless communications, for example, Bluetooth® technology.

In one embodiment, the at least one foot pedal 45 comprises a first foot pedal 46 and a second foot pedal 47, wherein the first foot pedal 46 controls an injection mode and the second foot pedal 47 controls an aspiration mode. The first and second foot pedals 46, 47 are preferably adjacent to one another and linked on a common platform to be operated by a single foot. Alternatively, the first and second foot pedals 46, 47 may be disposed separately such that the first foot pedal 46 is operated by the left foot of a user and the second foot pedal 47 is operated by the right foot.

In another embodiment, the first foot pedal 46 includes a potentiometer 48 to control the injection flow rate and the second foot pedal 47 includes a potentiometer 49 to control the aspiration flow rate. These potentiometers 48, 49 are preferably calibrated to respond in the same manner to the same delta reflecting the change in rotation of each foot pedal. This ensures that the aspiration rate is close to or the same as the injection rate.

In still another embodiment, the degree of rotation of the first foot pedal is proportional to the injection flow rate and the degree of rotation of the second foot pedal is proportional to the aspiration flow rate.

In a further embodiment, the at least one foot pedal 45 comprises a single foot pedal 46, wherein the single foot pedal 46 comprises a lever that rotates forward and backward about a pivot point from a resting position to switch between an aspiration and an injection mode.

In an alternative embodiment, the single foot pedal 46 includes a first potentiometer 48 to control the aspiration flow rate and a second potentiometer 49 to control the injection flow rate.

In yet another embodiment, the control unit 55 further comprises a first controller 56 to adjust the injection flow rate and a second controller 57 to adjust the aspiration flow rate. The controllers 56, 57 accomplish this by changing the conversion ratio of voltage from the foot pedals 46, 47 to electrical pulses emitted by the control unit 55. In still a further embodiment, the syringe driver includes a forward safety buffer 80. As used herein, a "forward safety buffer" 80 prevents the moving platform that supports the plunger 25 from contacting the base 65 that holds the syringe body 15 when the plunger 25 approaches the end of its forward stroke. This forward safety buffer 80 is carried on the base 65 and interfaces with a first end of a safety stopper 85 carried on the platform 60 in order to prevent the platform 60 from crashing into the base 65.

In another embodiment, the syringe driver includes a rear safety buffer 90. As used herein, a "rear safety buffer" 90 prevents the moving platform that supports the plunger 25 from contacting the step motor 50 at the end of the linear bearing 70 when the platform 60 approaches the end of its rearward stroke. This rear safety buffer 90 is carried on the step motor 50 and interfaces with a second end of the safety stopper 85 carried on the platform 60 in order to prevent the platform 60 from crashing into the step motor 50.

Figure 5A:
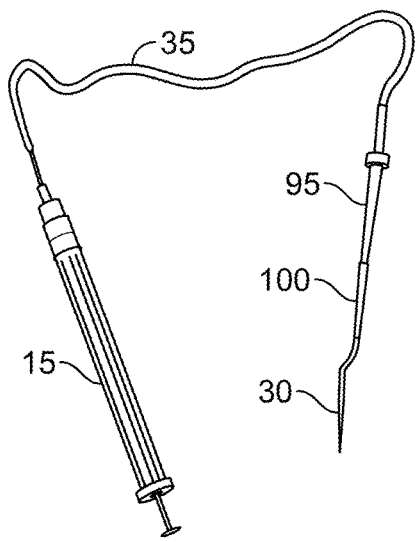
FIG. 5 are images of an exemplary device of the invention. (a) Assembled glass syringe with tubing, reservoir, and cannula. (b) Motorized syringe-driver with syringe mounted. (c) Dual foot pedal to operate the motorized syringe driver. Pressing either pedal drives the syringe plunger backward (aspiration) or forward (ejection). (d) Close-up of the cannula and connecting tubing showing the islets packed at the back of the cannula. This configuration allows delivery of the islets into the anterior chamber of the eye in a minimal volume to reduce reflux and loss of islets.

In another embodiment, as shown in FIG. 5(a) in the Example section, the motorized injection and aspiration system further comprises a reservoir 95 having first and second ends, wherein the reservoir's first end is connected to the syringe tube 35 and the reservoir's second end is connected to the cannula 30. In yet another embodiment, the reservoir 95 is connected to the cannula via a connecting tube 100.

As used herein, a "reservoir" is a vessel for holding tissues or fluids to be transplanted. In one embodiment, the reservoir comprises a pipette tip, preferably in the range of 250-300 µL. The reservoir 95 is preferably connected at one end to syringe tube 35 through a press fit configuration.

In a second aspect, the present invention also provides a method for utilizing the motorized injection and aspiration system 10, where the method comprises: (a) loading a syringe driver 40 with a syringe 15, wherein the syringe 15 is prefilled with a solution, and wherein the syringe 15 comprises a syringe body, a plunger 25, and a needle 20, and wherein the syringe driver 40 comprises a base 65 for holding the syringe body in a static position and a moveable platform 60 for receiving the plunger 25, (b) rotating a first foot pedal 46 forward from a resting position, (c) in response, driving the plunger 25 forward via the moveable platform 60 in an injection mode, (d) rotating a second foot pedal 47 forward from a resting position, and (e) in response, driving the plunger 25 backward via the moveable platform 60 in an aspiration mode.

Loading a syringe driver comprises placing the syringe body 15 in the channel 66 defined in the base 65, while aligning the plunger 25 with receptacle 75 defined by platform 60. A top plate 67 or other retaining means is then affixed to the base 65 by a set screw 68, for example, to hold the prefilled syringe 15 in place.

As used herein, "rotating" the foot pedal refers to any type of movement of the foot pedal 45 sufficient to move from a resting position. The point about which the first and second foot pedals pivot is preferably located at the end nearest the user, such that when a foot applies downward pressure the end furthest from the user rotates downward towards the floor and then rotates upward as pressure is decreased. In practice, the pivot point could be located at any location along the first and second foot pedals 46, 47.

As used herein, "driving the plunger" forward and backward via the moveable platform 60 is accomplished through the communication between the first and second foot pedals 46, 47, the control unit 55, the step motor 50 and the syringe driver 40 as discussed above. The platform 60 is carried on a linear bearing 70, which is driven by the step motor 50.

In one embodiment the method further comprises the step of coupling a first end of a tube 35 to the needle 20 and a second end of the tube 35 to a cannula 30. For instance, the tube 35 may be press fit over the end of the needle 20 and/or the cannula 30 or the tube 35 may be press fit within a hollow needle 20 and/or within a receiving end of a large diameter cannula 30. Alternatively, the tube 35 may be compressed over the end of the needle 20 and/or cannula 30 via clamps or any other securing means commonly known in the art.

In another embodiment the method further comprises the step of adjusting an injection flow rate by changing the degree of rotation of the first foot pedal 46. In a further embodiment the method further comprises the step of adjusting an aspiration flow rate by changing the degree of rotation of the second foot pedal 47. Specifically, the greater the angle of rotation of the first or second foot pedal 46, 47, the greater the flow rate and vice versa.

In a third aspect, the present invention provides a method for utilizing the motorized injection and aspiration system 10, where the method comprises: (a) loading a syringe driver 40 with a syringe 15, wherein the syringe 15 is prefilled with a solution, and wherein the syringe comprises a syringe body, a plunger 25, and a needle 20, and wherein the syringe driver 40 comprises a base 65 for holding a syringe body in a static position and a moveable platform 60 for receiving the syringe plunger 25, (b) rotating a single foot pedal 45 forward from a resting position, (c) in response, driving the plunger 25 forward via the moveable platform 60 in an injection mode, (d) rotating the single foot pedal 45 backward from a resting position, and (e) in response, driving the plunger 25 backward via the moveable platform 60 in an aspiration mode.

In one embodiment, the method further comprises the step of coupling a first end of a tube 35 to the needle 20 and a second end of the tube 35 to a cannula 30 as discussed above.

In an additional embodiment, the method further comprises the step of adjusting the injection flow rate by altering the degree of the foot pedal's forward rotation and adjusting the aspiration flow rate by altering the degree of the foot pedal's backward rotation.

In a fourth aspect, the present invention provides a method for utilizing the motorized injection and aspiration system 10, where the method comprises: (a) loading the syringe driver 40 with a syringe 15, wherein the syringe 15 is prefilled with a solution, and wherein the syringe 15 comprises a syringe body, a plunger 25, and a needle 20, and wherein the syringe driver 40 comprises a base 65 for holding the syringe body 15 in a static position and a moveable platform 60 for receiving the plunger 25, (b) rotating the first foot pedal 46 forward from a resting position, (c) in response, driving the plunger 25 forward via the moveable platform 60 in an injection mode, (d) rotating the second foot pedal 47 forward from a resting position, and (e) in response, driving the plunger 25 backward via the moveable platform 60 in an aspiration mode.

In a fifth aspect, the present invention provides a method for utilizing the motorized injection and aspiration system 10, where the method comprises: (a) loading a syringe driver 40 with a syringe 15, wherein the syringe 15 is prefilled with a solution, and wherein the syringe 15 comprises a syringe body, a plunger 25, and a needle 20, and wherein the syringe driver 40 comprises a base 65 for holding a syringe body 15 in a static position and a moveable platform 60 for receiving the syringe plunger 25, (b) rotating the single foot pedal 45 forward from a resting position, (c) in response, driving the plunger 25 forward via the moveable platform 60 in an injection mode, (d) rotating the single foot pedal 45 backward from a resting position, and (e) in response, driving the plunger 25 backward via the moveable platform 60 in an aspiration mode.

In a sixth aspect, the present invention provides a method for utilizing the motorized injection and aspiration system 10 to perform cell transplantation into the anterior chamber of the eye, where the method comprises: (a) loading the syringe driver 40 with a syringe 15, wherein the syringe 15 is prefilled with a solution and wherein the syringe 15 comprises a syringe body, a plunger 25, and a needle 20, and wherein the syringe driver 40 comprises a base 65 for holding the syringe body 15 in a static position and a moveable platform 60 for receiving the plunger 25, (b) aspirating a desired amount of islets/cells into a reservoir 95 using a syringe driver 40, (c) connecting the cannula 30 to the reservoir 95 via the connecting tube 100, (c) loading the cannula 30 with islets/cells by pushing the cells out of the reservoir 95 into the connecting tube 100 and then into the cannula 30, (e) connecting the second end of the syringe tube 35 to the needle 20, (f) making an incision in the cornea of the eye of a subject, (g) inserting the cannula 30 through the incision, (h) rotating the first foot pedal 46 forward from a resting position, (i) in response, driving the plunger 25 forward via the moveable platform 60 in an injection mode, ejecting the islets/cells out of the cannula 30 and depositing the cells on the iris, (j) if necessary, rotating the second foot pedal 47 forward from a resting position, (k) if necessary, in response, driving the plunger 25 backward via the moveable platform 60 in an aspiration mode, pulling the islets/cells back into the cannula 30, and (l) retracting the cannula 30 from the incision.

The subject can be any suitable subject in which islets/cells can be transplanted into the anterior chamber of the eye, including but not limited to mice, monkeys, rabbits, dogs, rats, pigs, and humans (for therapeutic treatment).

The methods of the invention may be used, for example, for cell transplantation to aid in disease treatment, or for drug development assays, such as those disclosed in, for example, US-2009-0060843, incorporated by reference herein in its entirety.

Any suitable cell type can be transplanted into the eye using the methods of the invention, including but not limited to endocrine cells (including but not limited to pancreatic beta (β) cells), embryonic tissue (pancreatic buds), renal glomeruli, and cells derived from any tissue type, including but not limited to fat, muscle, brain, liver, kidney, heart, and lungs. The cells to be transplanted may be individual cells, a plurality of cells of the same type, or a plurality of different cell types, such as tissues/tissue portions.

In a preferred embodiment, the tissue comprises pancreatic islets. In a further preferred embodiment, the pancreatic islets comprise β cells. As used herein, "pancreatic islets" are any population of cells that contains pancreatic islet β cells. Such pancreatic islet β cell populations include the pancreas, isolated pancreatic islets of Langerhans ("pancreatic islets") and dissociated pancreatic β cells. Methods for pancreatic isolation are well known in the art, and methods for isolating pancreatic islets, can be found, for example, in Pileggi et al., Diabetes 50(9):1983-1991 (2001); Cejvan et al., Diabetes 52:1176-1181 (2003); Zambre et al., Biochem. Pharmacol. 57:1159-1164 (1999), and Fagan et al., Surgery 124:254-259 (1998), and references cited therein. Once implanted in the host eye, the beta cells in these islets begin to make and release insulin. In a further preferred embodiment, the pancreatic islets/cells are centered in a culture dish to condense them and make it easier to load them in cannula 30. In one embodiment, centering the pancreatic islets/cells comprises spinning the culture dish in narrow concentric rings. In one embodiment, the pancreatic islets are isolated using collagenase digestion followed by purification on density gradients as described by Pileggi et al., Diabetes 50(9):1983-1991 (2001). Isolated islets can be cultured overnight before transplantation, which may help allow the pancreatic islets and β cells to recover from the isolation procedure. This may be particularly beneficial when diabetes reversal is desired, as it promotes transplantation of surviving/robust islets.

The anterior chamber of the eye comprises the front portion of the eye, and includes the structure in front of the vitreous humor, as well as the cornea, iris, ciliary body, and lens. Transplantation of islets/cells into the anterior chamber of the eye can comprise placement of the islets/cells into any one or more of these anterior eye chamber compartments. In one non-limiting example, target cells are transplanted via injection through the cornea, allowing engraftment of the transplanted target cells onto the iris, permitting observation and imaging through the cornea.

Further, in a preferred embodiment, air bubbles are flushed out of the reservoir 95 by rotating the first foot pedal 46 forward driving the syringe driver 40 forward to ensure a continuous stream of islets when aspirating into the reservoir 95. After flushing air bubbles out of the reservoir 95, aspiration of islets/cells is accomplished by rotating the second foot pedal 47 to drive the syringe driver 40 backward. As islets are aspirated into the reservoir 95, they will tend to swirl and will remain together at the bottom of the reservoir 95. Once the islets are in the reservoir 95, the cannula 30 is connected to the reservoir 95 via connecting tube 100. Cannula 30 is then loaded with islets by again rotating the first foot pedal 46 forward to push the islets out of the reservoir 95 into the tube 35 and then into the cannula 30.

In a preferred embodiment, transplantation is performed under anesthesia, preferably generalized anesthesia. Anesthetizing the subject is done using any suitable method, including but not limited to use of an oxygen/isoflurane mixture (1.5-3%) inhalation, when the subject is a mouse. Alternative anesthetic techniques are well known to those of skill in the art.

In a preferred embodiment, the eyelid of an eye is retracted to make the incision, though there may instances in which the subject has no eyelid. When preparing the eye for the procedure, making an incision in the cornea of the eye (preferably a single incision) may comprise penetrating only the tip of a scalpel into the cornea and slashing the cornea to one side if needed. In a preferred embodiment, making the incision comprises incising the cornea laterally at a midpoint between the apex of the cornea and limbus. In one embodiment, the scalpel may comprise a disposable insulin syringe (29-31 G). Surgical sharp scalpels may not require slashing to make the incision, simple penetration of the sharp scalpel tip may be sufficient.

During the transplantation, as the plunger 25 is driven forward and the islets are ejected out of the cannula 30 and deposited on the iris, the ejection should occur using the syringe driver 40 in brief thrusts in as little volume(s) as possible in the quadrant opposite to the incision. This will help avoid islet backflow (reflux) due to excessive pressure buildup. These brief thrusts can be accomplished by compacting islets to ensure they remain together in the connecting tube 100/cannula 30, in one embodiment, by flicking or tapping the connecting tubing 100 as the tube 100 and cannula 30 are loaded with islets from the reservoir 95. In one embodiment, the flicking or tapping is ceased once all the air bubbles ahead of the islets exit the tip of the cannula 30. In another embodiment, the flicking or tapping is ceased as the islets enter the back of the cannula 30. Any remaining air bubbles ahead of the islets can help prevent reflux of islets out of the anterior chamber of the eye and will dissipate overnight. Further, in one embodiment, the tip of the cannula 30 may be placed into the culture dish while islets are being loaded into the cannula 30 from the reservoir 95 in order to capture any islets prematurely forced from the cannula 30.

The plunger will only need to be driven backwards to aspirate the islets and pull them back into the cannula 30, if recovery of islets inside or outside the anterior chamber is desired for reasons including but not limited to, change in transplanted islet mass, islets end up in wrong location, and reflux out of the anterior chamber. Retracting the cannula 30 from the incision is a useful step if a large volume of islet-containing medium was injected as islet reflux may be inevitable. In order to eliminate and/or minimize islet reflux, the cannula 30 may be gently rotated while inside the incision in the anterior chamber of the eye to release excess pressure through the incision around the cannula 30. The operator should check for signs of reflux while attempting to retract the cannula 30 and, if needed, wait until pressure inside the anterior chamber subsides before completely retracting the cannula 30.

All embodiments of the motorized injection and aspiration system of the invention can be used in the methods of the second and sixth aspects of the invention.

Note that any of the foregoing embodiments of any aspect may be combined together to practice the claimed invention. The Examples that follow are illustrative of specific embodiments of the invention, and various uses thereof. They are set forth for explanatory purposes only, and should not be construed as limiting the scope of the invention in any way.

EXAMPLES

Presented below, is a new approach combining intraocular transplantation and confocal microscopy enables longitudinal, non-invasive real-time imaging with single-cell resolution within grafted tissues in vivo. This demonstrates how to transplant pancreatic islets into the anterior chamber of the mouse eye.

Advances in intravital microscopy have revealed physiological phenomena not predicted by in vitro studies (Weigert et al., 2010). This highlights the challenge in translating findings obtained by conventional in vitro methods into the living animal. In the last decade, visualization of tissues in living animals was considerably improved by technological advances in imaging modalities (reviewed in (Aswathy et al., 2010; Ghoroghchian et al., 2009; Leibiger et al., 2011; Ntziachristos, 2010; Wang et al., 2010b)). This has spurred a need for in vivo imaging approaches with feasible application in experimental animal models to enable non-invasive visualization of target tissues non-invasively.

Techniques such as magnetic resonance imaging and positron emission tomography or bioluminescence (Prescher et al., 2010) have enabled non-invasive imaging of organs/tissues deep within the body (Leblond et al., 2010; Toso et al., 2008). But these techniques cannot achieve single cell-resolution due to high background signals and low spatial resolution, despite the use of high contrast materials or tissue-specific luminescence (Ntziachristos, 2010). This was addressed with the advent of two-photon fluorescence confocal microscopy (Denk et al., 1990). Two-photon microscopy enabled intravital imaging studies to visualize and quantify cellular events with unprecedented details (Denk et al., 1994; Wang et al., 2010a). This has lead to the characterization of key biological processes in health and disease (Cahalan and Parker, 2008; Celli et al., 2011; Khorshidi et al., 2011; Matheu et al., 2011). While pioneering intravital imaging studies have primarily "mimicked" in vivo conditions in excised tissue (e.g., lymph nodes), other studies have used invasive approaches to image exposed target tissues in situ (Coppieters et al., 2010; Fan et al., 2010; Martinic and von Herrath, 2008; Mostany and Portera-Cailliau, 2008; Sabek et al., 2010).

It was recently demonstrated that combining high-resolution confocal microscopy with transplantation into the anterior chamber of the eye (ACE) provides a powerful and versatile imaging platform in vivo (Speier et al., 2008a; Speier et al., 2008b). This approach enabled studying the physiology of pancreatic islets with single cell-resolution non-invasively and longitudinally (Speier et al., 2008a; Speier et al., 2008b). This model was used to study auto-immune responses during development of type 1 diabetes in animal models (unpublished data). It was also used to study pancreatic development, as well as, in studies of kidney function by transplanting individual glumeruli in the ACE (unpublished data). A recent report using this approach further demonstrated its application to study immune responses after transplantation of pancreatic islets into the ACE (Abdulreda et al., 2011). Importantly, this study showed that transplantation into the anterior chamber of the eye provides a natural body window to perform: (i) longitudinal, non-invasive imaging of transplanted tissues in vivo; (ii) in vivo cytolabeling to assess cellular phenotype and viability in situ; (iii) real-time tracking of infiltrating immune cells in the target tissue; and (iv) local intervention by topical application or intraocular injection.

Following is a description of an exemplary technique for performing transplantation into the anterior chamber of the eye using pancreatic islets. The procedure is performed under the stereoscope in 2 steps, the first step involves loading the islets into the cannula and the second step is the actual transplantation into the ACE.

1) Loading Islets in Cannula for Transplantation 1.1) Center islets in culture dish by spinning the dish in narrowing concentric circles.

1.2) Disconnect the cannula (25 G; BD Ophthalmic Systems Ref 58517) from the "reservoir" and place the cannula and connecting tubing on a clean surface. The reservoir can be made out of a 300 μL disposable plastic pipette tip without filter (FIG. 5*a*).

Figure 5B:
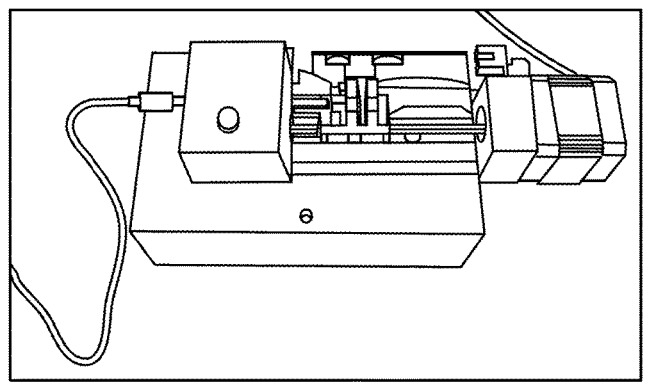
Figure 5C:
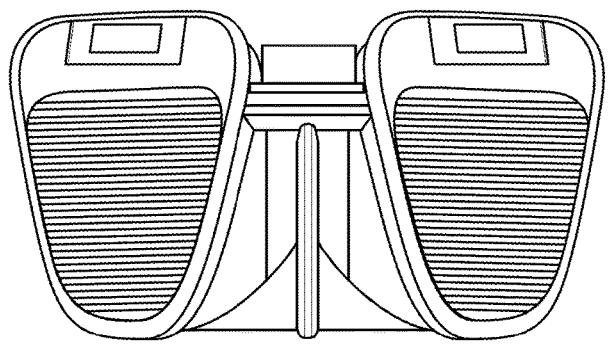

1.3) Flush air bubbles (if any) out of the reservoir to ensure continuous stream of islets when aspirating into reservoir. Flushing the reservoir is done by driving forward the hands-free motorized syringe-driver using the foot pedal (FIG. 5*b,c*). This will also make space in the syringe to allow aspiration of the islets into the reservoir (pre-loaded with sterile solution such as saline, PBS or culture media).

1.4) Gently aspirate desired amount of islets into the reservoir. Islets will tend to swirl as they enter the reservoir and will remain together towards the bottom of the reservoir. Aspiration is done by driving backward the motorized syringe-driver using the foot pedal.

1.5) Reconnect the cannula to the reservoir via the connecting tubing.

Figure 5D:
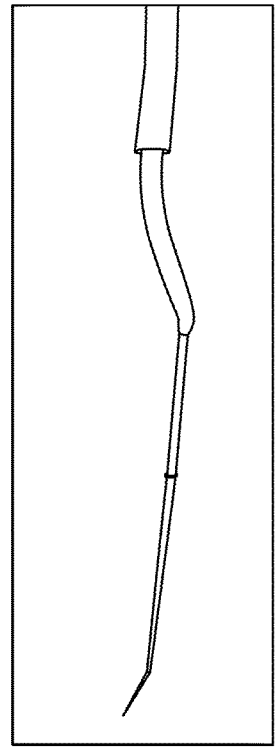

1.6) Place the cannula tip back in the culture dish and flush the islets out of the reservoir into the tubing then into the cannula. Ensure that islets remain together as the tubing/cannula is back-filled by gently "flicking" (tapping) the tubing (FIG. 5*d*). Stop either before or after all air bubbles ahead of the islets are flushed out the cannula. If not sure, stop as islets enter the back of the cannula. Remaining air bubbles ahead of islets can help prevent reflux (backflow) of islets out of the ACE and will dissipate overnight.

2) Islet Transplantation into the Anterior Chamber of the Eye 2.1) Position the anesthetized mouse on a pad under stereoscope.

Figure 6A:
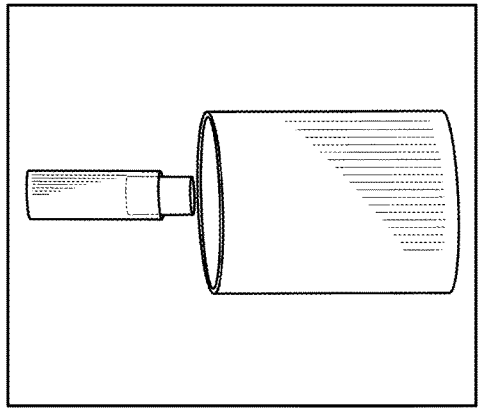
FIG. 6 is an exemplary depiction of the transplantation procedure into the anterior chamber of the eye (ACE). (a) Photograph of the mouse anesthesia mask. (b) Close-up view of the anesthesia mask made from a 1 ml disposable plastic pipette tip without filter. Several holes were made in the tip to allow mixing of oxygen with isoflurane before reaching the mouse. (c) Close-up view showing the eye to be transplanted "popped" out for better access. The eye is "popped" out by stretching the skin of the head using the thumb and index finger. (d) Schematic depiction of the transplantation procedure highlighting the location of the incision at midpoint between the apex of the cornea and the limbus. The cannula is inserted through the incision to deliver the islets into the ACE. Islets are deposited on top of the iris where they engraft.
Figure 6B:
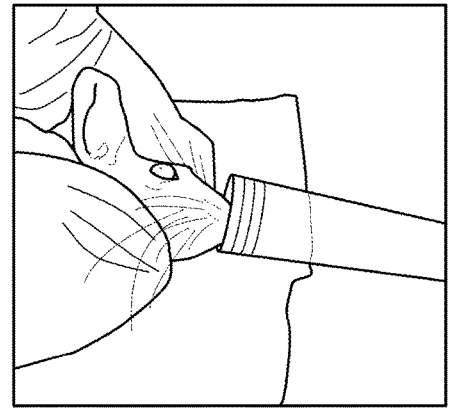

2.2) Place the snout of the mouse into anesthesia "mask" connected to oxygen/isoflurane anesthesia machine. The mask is made out of a 1 ml disposable plastic pipette tip (without filter) and connected to anesthesia tubing through the narrow end (FIG. 6a,b).

Figure 6C:
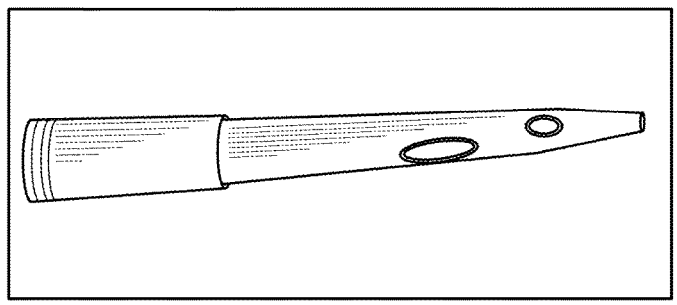

2.3) Gently retract the eye lids of the eye to be transplanted using the index finger and thumb of the free hand and "pop" the eye out for better exposure and easy access (FIG. 6c). This requires some practice to perfect without impeding breathing of the mouse by excessive pressure on the neck or blocking blood flow to the head.

Figure 6D:
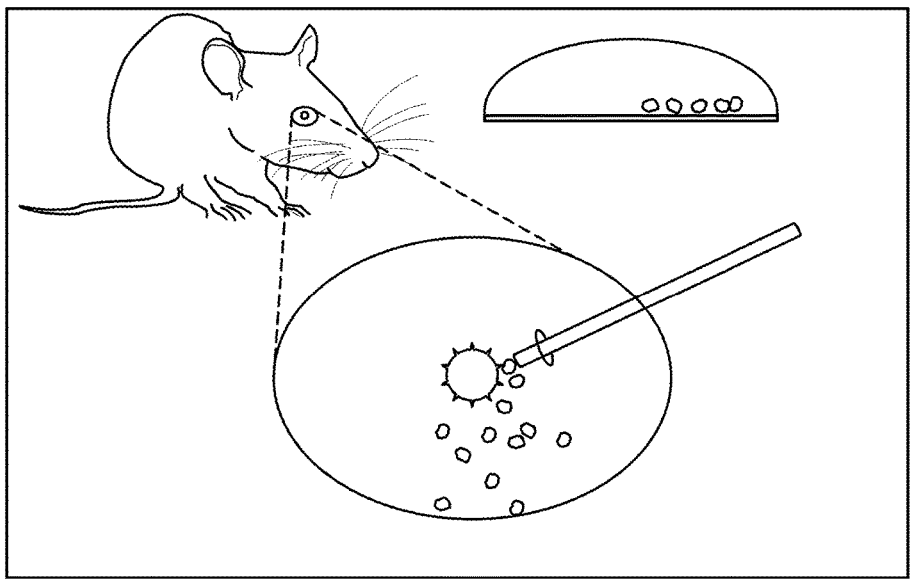

2.4) Using a disposable insulin syringe (29-31 G) as scalpel, make a single incision in the cornea by penetrating only the tip and "slashing" the cornea to one side to make the incision laterally. Make the incision at midpoint between the apex of the cornea and limbus to minimize reflux of the islets out of the ACE (FIG. 6d).

2.5) Carefully insert the cannula (preloaded with islets) through the incision.

2.6) Slowly eject islets out of the cannula and deposit on top of the iris. To avoid islet reflux due to excessive pressure buildup, eject the islets in brief thrusts in as little volume(s) as possible in the quadrant opposite to the incision to minimize islet reflux. This can be ensured by compacting islets in the tubing/cannula as they are flushed out of the reservoir into the cannula (see step 1.6).

2.7) Slowly retract the cannula out of the anterior chamber. This is a useful step if a large volume of islet-containing medium was injected as islet reflux due to pressure build up inside the ACE may be inevitable. To eliminate/minimize islet reflux, gently rotate the cannula while inside the ACE to release excess pressure through the incision around the cannula. Check for signs of reflux as the cannula is retracted and, if needed, wait until pressure subsides before completely retracting the cannula out of the ACE.

2.8) Inject buprenorphine for analgesia (0.05-0.1 mg/kg, subcutaneously) for the first 48 h as needed.

2.9) Apply erythromycin ophthalmic antibiotic ointment to the transplanted eye.

2.10) Place the animal back in a warmed cage to allow recovery from anesthesia.

Figure 7:
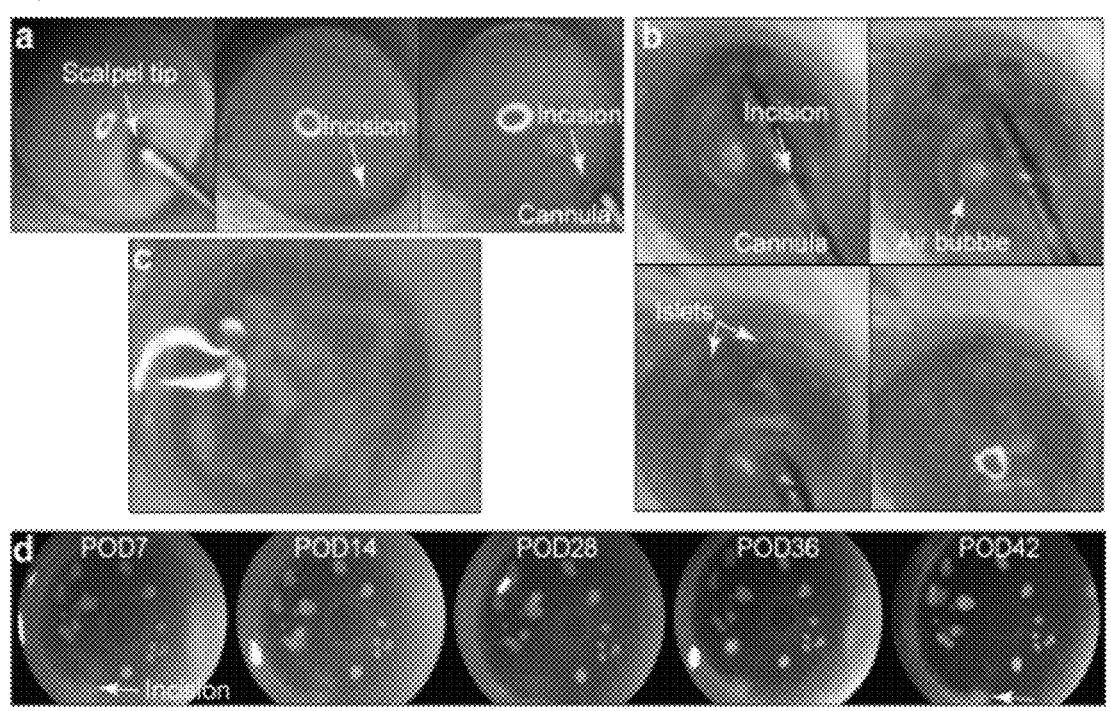
FIG. 7 provides representative images of transplantation procedures performed according to the methods of the invention. (a) Series of images showing how far the tip of the scalpel (needle) is pushed into the cornea while making the incision. A small incision is made without bleeding. The incision is slightly larger than the cannula. (b) Series of images showing islets being ejected out of the cannula while using an air bubble to prevent reflux. (c) Representative image of a transplanted eye highlighting the clarity of the ACE immediately after transplantation. (d) Series of images of the same eye acquired on the specified post operative days (POD) highlighting the preferred location of islets for in vivo imaging and how well the incision healed and the clarity of the cornea at 6 weeks after transplantation.

Representative Results:

There are a few parameters that define a "good" transplantation. A good transplantation is one that proceeds without bleeding when making the incision. Bleeding is prevented by penetrating only the tip of the scalpel (needle) into the ACE (FIG. 7a). This also helps prevent puncturing the iris and ensures a small incision that heals very well without causing cloudiness of the cornea over time (FIG. 7c, d). Another useful aspect to a successful transplantation is to be able to transplant the total desired amount of islets without loss due to reflux out of the ACE. As mentioned in the protocol step 1.6, this can be minimized by ejecting the islets in the least possible volume and, if needed, by using an air bubble to help seal the incisions upon retracting the cannula (FIG. 7b). Moreover, delivering the islets on top of the iris between the edge of the pupil and the limbus positions the islets in a location very amenable for in vivo imaging (FIG. 7d). From practical perspective, having the islets at this intermediate position reduces the thickness of the imaging z-stacks required to span whole islets.

Discussion:

Murine pancreatic islets were isolated using collagenase digestion followed by purification on density gradients, as described previously (Pileggi et al., 2001). Isolated islets were cultured overnight before transplantation. While this may not be required, it is recommended to allow the islets to recover from the isolation procedure. This is particularly useful, for example, when transplantation is performed in diabetic recipients as it ensures transplantation of surviving/robust islets for better glycemic control.

Transplantation is performed under generalized anesthesia with oxygen/isoflurane mixture (1.5-3%) inhalation to effect. Alternative inhalation or injection anesthetics (e.g., ketamine) can be used. If injection anesthesia is used, skip step 2.2 in the protocol. In some mice, it is possible to break blood vessels when making the incision in the typically avascular cornea. For example, the cornea of nude mice tends to be vascularized. Avoid vascularized areas when possible. Use a new syringe per incision. Avoid puncturing the iris with the needle when making the incision. Preventing contact with the iris can be enhanced by facing the beveled side of the needle tip toward the iris. Do not dry/aspirate aqueous humor after making the incision. It is easier to penetrate the cannula through the incision in a "wet" cornea; add a few drops of sterile PBS or culture media to cornea if needed. Postoperative analgesia can be obtained by injecting subcutaneously buprenorphine (0.05-0.1 mg/kg) or preferred analgesic(s) for the first 48 h as needed. Alternative ophthalmic antibiotics can be used as well.

In this study, a custom-built microinjection apparatus operated via a foot pedal to drive the 100 µL syringe (Hamilton, Nev.) to aspirate (load) and eject the islets out of the cannula into the ACE was used (FIG. 5). This can be substituted with any 100 µL gas-tight glass syringe with a screw-driven plunger that can be operated manually to aspirate/eject the islets; this however will likely require the assistance of another person to operate. In either case, although not required we recommend pre-loading the assembled syringe, tubing, and reservoir with a sterile solution (saline, PBS or culture media) to ensure smooth aspiration and ejection of the islets. This is particularly useful if/when the packed islets clog the cannula.

Transplantation procedures are typically performed under clean conditions inside a biosafety cabinet without risk of infections. All used solutions, syringes, cannula, tubing, and gauze are autoclaved or gas-sterilized.

It is demonstrated herein how to transplant pancreatic islets into the ACE for imaging purposes where fewer islets are needed to transplant. In the case where diabetes reversal is desired in the recipient animal, a larger amount of islets needs to be transplanted. However, particular attention should be paid to steps 2.6 and 2.7 in the protocol to avoid loss of transplanted islets due to reflux. The transplantation procedure can be performed in ~5 min per mouse. This technique can be used to transplant a variety of tissues into the anterior chamber of the eye. As mentioned above, we have transplanted renal glomeruli as well as embryonic tissue (pancreatic buds) to study pancreatic development in the anterior chamber of the eye in vivo.

Table of Specific Reagents and Equipment:

| Name of reagent | Company | Catalogue number | Comments |
| --- | --- | --- | --- |
| Cannula; Tapered Hydrodelineator [Blumenthal] 0.5 × 22 mm (25 G × ⅞ in) 45° | BD Visitec (BD Ophthalmic Systems) | 585107 | Different diameter cannulas may be used as needed |
| Reservoir | Bioclean | GPS-L300 | Custom-built from 300 µL Pipette tip (without filter) |
| Anesthesia mask | Bioclean | GPS-L1000 | Custom-built from 1000 µL Pipette tip (without filter) |
| Motorized injection system with adjustable and reversible flow rate | Biocrine | Contact corresponding author for more information | (Motorized-syringe driver). Patent pending; Ser. No. 61/485,793 |
| Glass syringe | Hamilton | 81020 | 100 µL. Gas-tight |
| Tubing | Tygon | AAQ04103 | Connects syringe to reservoir. 0.02 × 0.06 in (formulation S-54-HL) |
| Connecting tubing | Scientific Commodities Inc. | BB31785-V/3A | Connects reservoir to cannula. 0.027 × 0.045 in (85 Durometer Vinyl) |
| Connecting tubing | Sani-tech | STHT-C-025-0 (104583) | Coupler between reservoir and connecting tubing. 0.025 × 0.11 in (ID × Wall) |
| Insulin syringe | BD | 309301 | 29 G ½ in (³⁄₁₀ cc) |
| Anesthesia machine | Surgivet | Model 100 Vaporizer | |
| IsoTHESIA (Isoflurane) | Buttler Animal Health Supply | 11695-6775-2 | 99.9% Isoflurane/ml |
| Ketaset (Ketamine HCL) | Fort dodge Animal Health | 0856-2013-01 | Alternative injectable anesthesia |
| Beprenex (Buprenorphine HCL) | Reckitt Benckiser Health Care (UK) Ltd. | 12496-075-7-1 | 0.3 mg/ml |
| Erythromycin Ophthalmic Ointment USP, 0.5% | Akron | 17478-070-35 | Applied prophylactically to transplanted eye |
| 0.9% Sodium Chloride (Saline) | Hospira Inc. | 0409-7983-03 | For iv injection. Sterile |
| PBS | Gibco | 10010-023 | 1X. Sterile |
| CMRL medium 1066 | Cellgro | 98-304-CV | Supplemented, CIT modification. Preferred media for islets |

REFERENCES

Abdulreda, M. H., Faleo, G., Molano, R. D., Lopez-Cabezas, M., Molina, J., Tan, Y., Echeverria, O. A., Zahr-Akrawi, E., Rodriguez-Diaz, R., Edlund, P. K., et al. (2011). High-resolution, noninvasive longitudinal live imaging of immune responses. In Proc Natl Acad Sci USA.

Aswathy, R. G., Yoshida, Y., Maekawa, T., and Kumar, D. S. (2010). Near-infrared quantum dots for deep tissue imaging. Anal Bioanal Chem 397, 1417-1435.

Cahalan, M. D., and Parker, I. (2008). Choreography of cell motility and interaction dynamics imaged by two-photon microscopy in lymphoid organs. Annu Rev Immunol 26, 585-626.

Celli, S., Albert, M. L., and Bousso, P. (2011). Visualizing the innate and adaptive immune responses underlying allograft rejection by two-photon microscopy. Nat Med.

Coppieters, K., Martinic, M. M., Kiosses, W. B., Amirian, N., and von Herrath, M. (2010). A novel technique for the in vivo imaging of autoimmune diabetes development in the pancreas by two-photon microscopy. PLoS One 5, e15732.

Denk, W., Delaney, K. R., Gelperin, A., Kleinfeld, D., Strowbridge, B. W., Tank, D. W., and Yuste, R. (1994). Anatomical and functional imaging of neurons using 2-photon laser scanning microscopy. J Neurosci Methods 54, 151-162.

Denk, W., Strickler, J. H., and Webb, W. W. (1990). Two-photon laser scanning fluorescence microscopy. Science 248, 73-76.

Fan, Z., Spencer, J., Lu, Y., Pitsillides, C., Singh, G., Kim, P., Yun, S., Toxavidis, V., Strom, T., Lin, C., et al. (2010). In vivo tracking of 'color-coded' effector, natural and induced regulatory T cells in the allograft response. Nat Med 16, 718-722.

Ghoroghchian, P. P., Therien, M. J., and Hammer, D. A. (2009). In vivo fluorescence imaging: a personal perspective. Wiley Interdiscip Rev Nanomed Nanobiotechnol 1, 156-167.

Khorshidi, M. A., Vanherberghen, B., Kowalewski, J. M., Garrod, K. R., Lindstrom, S., Andersson-Svahn, H., Brismar, H., Cahalan, M. D., and Onfelt, B. (2011). Analysis of transient migration behavior of natural killer cells imaged in situ and in vitro. Integr Biol (Camb) 3, 770-778.

Leblond, F., Davis, S., Valdés, P., and Pogue, B. (2010). Pre-clinical whole-body fluorescence imaging: Review of instruments, methods and applications. J Photochem Photobiol B 98, 77-94.

Leibiger, I. B., Caicedo, A., and Berggren, P. O. (2011). Non-invasive in vivo imaging of pancreatic β-cell function and survival—a perspective. Acta Physiol (Oxf).

Martinic, M. M., and von Herrath, M. G. (2008). Real-time imaging of the pancreas during development of diabetes. Immunol Rev 221, 200-213.

Matheu, M. P., Cahalan, M. D., and Parker, I. (2011). Immunoimaging: studying immune system dynamics using two-photon microscopy. Cold Spring Harb Protoc 2011, pdb top99.

Mostany, R., and Portera-Cailliau, C. (2008). A method for 2-photon imaging of blood flow in the neocortex through a cranial window. J Vis Exp.

Ntziachristos, V. (2010). Going deeper than microscopy: the optical imaging frontier in biology. In Nat Methods (United States), pp. 603-614.

Pileggi, A., Molano, R. D., Berney, T., Cattan, P., Vizzardelli, C., Oliver, R., Fraker, C., Ricordi, C., Pastori, R. L., Bach, F. H., et al. (2001). Heme oxygenase-1 induction in islet cells results in protection from apoptosis and improved in vivo function after transplantation. Diabetes 50, 1983-1991.

Prescher, A., Mory, C., Martin, M., Fiedler, M., and Uhlmann, D. (2010). Effect of FTY720 treatment on postischemic pancreatic microhemodynamics. Transplant Proc 42, 3984-3985.

Sabek, O., Gaber, M. W., Wilson, C. M., Zawaski, J. A., Fraga, D. W., and Gaber, O. (2010). Imaging of human islet vascularization using a dorsal window model. In Transplant Proc (United States: Published by Elsevier Inc.), pp. 2112-2114.

Speier, S., Nyqvist, D., Cabrera, O., Yu, J., Molano, R. D., Pileggi, A., Moede, T., Köhler, M., Wilbertz, J., Leibiger, B., et al. (2008a). Noninvasive in vivo imaging of pancreatic islet cell biology. Nat Med 14, 574-578.

Speier, S., Nyqvist, D., Kohler, M., Caicedo, A., Leibiger, I. B., and Berggren, P. O. (2008b). Noninvasive high-resolution in vivo imaging of cell biology in the anterior chamber of the mouse eye. Nat Protoc 3, 1278-1286.

Toso, C., Vallee, J. P., Morel, P., Ris, F., Demuylder-Mischler, S., Lepetit-Coiffe, M., Marangon, N., Saudek, F., James Shapiro, A. M., Bosco, D., et al. (2008). Clinical magnetic resonance imaging of pancreatic islet grafts after iron nanoparticle labeling. Am J Transplant 8, 701-706.

Wang, B. G., Konig, K., and Halbhuber, K. J. (2010a). Two-photon microscopy of deep intravital tissues and its merits in clinical research. J Microsc 238, 1-20.

Wang, Y., Maslov, K., Kim, C., Hu, S., and Wang, L. (2010b). Integrated photoacoustic and fluorescence confocal microscopy. IEEE Trans Biomed Eng 57, 2576-2578.

Weigert, R., Sramkova, M., Parente, L., Amornphimoltham, P., and Masedunskas, A. (2010). Intravital microscopy: a novel tool to study cell biology in living animals. Histochem Cell Biol 133, 481-491.

While the invention has been described in terms of various embodiments, it is understood that variations and modifications will occur to those skilled in the art. Therefore, it is intended that the appended claims cover all such equivalent variations that come within the scope of the invention as claimed.

The invention claimed is:

1. A motorized injection and aspiration system comprising:
   a needle having first and second ends;
   a syringe coupled to the first end of the needle, wherein the syringe includes a plunger;
   a cannula having first and second ends;
   a reservoir having a first end and a second end;
   a tube having first and second ends, wherein the first end of the tube is coupled to the second end of the needle and the second end of the tube is coupled to the first end of the reservoir, and wherein the second end of the reservoir is coupled to the first end of the cannula and the second end of the cannula is a free end;
   a syringe driver to drive the plunger;
   at least one foot pedal having at least one potentiometer configured to control at least one of an injection flow rate and an aspiration flow rate based on a rotation angle of the at least one potentiometer;
   a step motor; and
   a control unit in communication with the step motor, the syringe driver and the at least one foot pedal.

2. The motorized injection and aspiration system of claim 1, wherein the at least one foot pedal comprises a first foot pedal and a second foot pedal, wherein the first foot pedal controls the injection mode and the second foot pedal controls the aspiration mode.

3. The motorized injection and aspiration system of claim 2, wherein the at least one potentiometer includes a first potentiometer and a second potentiometer, wherein the first foot pedal includes the first potentiometer to control the injection flow rate and the second foot pedal includes the second potentiometer to control the aspiration flow rate.

4. The motorized injection and aspiration system of claim 3, wherein a degree of rotation of the first foot pedal is proportional to the injection flow rate and a degree of rotation of the second foot pedal is proportional to the aspiration flow rate.

5. The motorized injection and aspiration system of claim 1, wherein the at least one foot pedal comprises a single foot pedal, wherein the single foot pedal comprises a lever that rotates forward and backward about a pivot point from a resting position to switch between an aspiration mode and an injection mode.

6. The motorized injection and aspiration system of claim 5, wherein the at least one potentiometer of the single foot pedal includes a first potentiometer to control the aspiration flow rate and a second potentiometer to control the injection flow rate.

7. The motorized injection and aspiration system of claim 1, wherein the control unit further comprises a first controller to adjust the injection flow rate and a second controller to adjust the aspiration flow rate.

8. The motorized injection and aspiration system of claim 1, wherein the syringe driver includes a forward safety buffer.

9. The motorized injection and aspiration system of claim 1, wherein the syringe driver includes a rear safety buffer.

10. The motorized injection and aspiration system of claim 1, wherein the syringe driver comprises a base for holding a syringe body in a static position and a moveable platform for receiving the syringe plunger.

11. The motorized injection and aspiration system of claim 1, wherein the syringe comprises a Luer-Lock-type syringe.

12. The motorized injection and aspiration system of claim 1, wherein the reservoir is connected to the cannula via a connecting tube.

13. A method for utilizing the motorized injection and aspiration system of claim 1 comprising:
   loading the syringe driver with the syringe, wherein the syringe is prefilled with a solution and wherein the syringe further comprises a syringe body, and wherein the syringe driver comprises a base for holding the syringe body in a static position and a moveable platform for receiving the plunger, and wherein the at least one foot pedal comprises a first foot pedal and a second foot pedal;

rotating the first foot pedal forward from a resting position;

in response, driving the plunger forward via the moveable platform in an injection mode;

rotating the second foot pedal forward from a resting position; and in response, driving the plunger backward via the moveable platform in an aspiration mode.

14. The method of claim 13, further comprising adjusting an injection flow rate by changing the degree of rotation of the first foot pedal.

15. The method of claim 13, further comprising adjusting an aspiration flow rate by changing the degree of rotation of the second foot pedal.

16. A method for utilizing the motorized injection and aspiration system of claim 1 comprising:

loading the syringe driver with the syringe, wherein the syringe is prefilled with a solution and wherein the syringe further comprises a syringe body, and wherein the syringe driver comprises a base for holding the syringe body in a static position and a moveable platform for receiving the syringe plunger, and wherein the at least one foot pedal comprises a single foot pedal;

rotating the single foot pedal forward from a resting position;

in response, driving the plunger forward via the moveable platform in an injection mode;

rotating the single foot pedal backward from a resting position;

and in response, driving the plunger backward via the moveable platform in an aspiration mode.

17. The method of claim 16, further comprising adjusting the injection flow rate by altering the degree of the foot pedal's forward rotation and adjusting the aspiration flow rate by altering the degree of the foot pedal's backward rotation.

18. A method for utilizing the motorized injection and aspiration system of claim 2, the method comprising:

loading the syringe driver with the syringe, wherein the syringe is prefilled with a solution and wherein the syringe further comprises a syringe body, and wherein the syringe driver comprises a base for holding the syringe body in a static position and a moveable platform for receiving the plunger;

rotating the first foot pedal forward from a resting position;

in response, driving the plunger forward via the moveable platform in an injection mode;

rotating the second foot pedal forward from a resting position; and in response, driving the plunger backward via the moveable platform in an aspiration mode.

19. A method for utilizing the motorized injection and aspiration system of claim 5, the method comprising:

loading the syringe driver with the syringe, wherein the syringe is prefilled with a solution and wherein the syringe further comprises a syringe body, and wherein the syringe driver comprises a base for holding a syringe body in a static position and a moveable platform for receiving the syringe plunger;

rotating the single foot pedal forward from a resting position;

in response, driving the plunger forward via the moveable platform in an injection mode;

rotating the single foot pedal backward from a resting position;

and in response, driving the plunger backward via the moveable platform in an aspiration mode.

20. A method for utilizing the motorized injection and aspiration system of claim 1 to perform cell transplantation into the anterior chamber of the eye, the method comprising:

loading the syringe driver with the syringe, wherein the syringe is prefilled with a solution and wherein the syringe further comprises a syringe body, and wherein the syringe driver comprises a base for holding the syringe body in a static position and a moveable platform for receiving the plunger, and wherein the at least one foot pedal comprises a first foot pedal and a second foot pedal;

aspirating a desired amount of cells into the reservoir using the syringe driver;

connecting the cannula to the reservoir via the connecting tube;

loading the cannula with cells by pushing the cells out of the reservoir into the connecting tube and then into the cannula;

making an incision in the cornea of the eye;

inserting the cannula through the incision;

rotating the first foot pedal forward from a resting position;

in response, driving the plunger forward via the moveable platform in an injection mode, ejecting the cells out of the cannula and depositing the cells on the iris;

rotating the second foot pedal forward from a resting position; in response, driving the plunger backward via the moveable platform in an aspiration mode, pulling the cells back into the cannula; and retracting the cannula from the incision.

21. The method of claim 13, wherein the method is used for cell transplantation into the eye.

22. The method of claim 21, wherein the cells comprise pancreatic β cells, and wherein the method is used for treatment of Type 1 diabetes.

* * * * *